(12) United States Patent
Kitamura

(10) Patent No.: US 8,148,542 B2
(45) Date of Patent: Apr. 3, 2012

(54) METHOD FOR PRODUCING CRYSTAL POLYMORPHS OF 2-(3-CYANO-4-ISOBUTYLOXYPHENYL)-4-METHYL-5-THIAZOLECARBOXYLIC ACID

(75) Inventor: Mitsutaka Kitamura, Himeji (JP)

(73) Assignee: Teijin Pharma Limited, Tokyo (JP)

( * ) Notice: Subject to any disclaimer, the term of this patent is extended or adjusted under 35 U.S.C. 154(b) by 193 days.

(21) Appl. No.: 12/306,170

(22) PCT Filed: Jun. 22, 2007

(86) PCT No.: PCT/JP2007/062593
§ 371 (c)(1),
(2), (4) Date: Dec. 22, 2008

(87) PCT Pub. No.: WO2007/148787
PCT Pub. Date: Dec. 27, 2007

(65) Prior Publication Data
US 2009/0203919 A1    Aug. 13, 2009

(30) Foreign Application Priority Data
Jun. 23, 2006    (JP) .................................. 2006-173774

(51) Int. Cl.
*C07D 277/56*    (2006.01)
(52) U.S. Cl. ...................................... 548/201
(58) Field of Classification Search .................... 548/201
See application file for complete search history.

(56) References Cited

U.S. PATENT DOCUMENTS
6,225,474 B1    5/2001    Matsumoto et al.

FOREIGN PATENT DOCUMENTS
| EP | 1 020 454 A1 | 7/2000 |
| JP | 2003-261548 A | 9/2003 |
| WO | 99/65885 A1 | 12/1999 |

OTHER PUBLICATIONS

Kitamura et al. Journal of Crystal Growth 2003, 257, 177-184.*
Kitamura et al. Journal of Crystal Growth 2002, 236, 676-686.*
Kitamura et al. Journal of Crystal Growth 2002, 237-239, 2205-2214.*
Pavia et al., Introduction to Organic Laboratory Techniques (1990), pp. 577-596.*
JW Mullin, Chapter 6 Crystal growth, Crystallization (2001), pp. 216-288.*
Armarego & Chai, Chapter 2 Chemical Methods Used in Purification, Purification of Laboratory Chemicals (5th ed. 2003), p. 63.*
Kitamura, et al., Effect of Temperature on Antisolvent Crystallization and Transformation Behaviors of Thiazole-Derivative Polymorphs, Crystal Growth & Design, 2006, 6(5), pp. 1214-1218.
Kitamura, Mitsutaka "Controlling Factors and Mechanism of Polymorphic Crystallization", Crystal Growth & Design, vol. 4, No. 6, pp. 1153-1159, 2004.
European Search Report dated Oct. 25, 2010, as issued in European Patent Application No. 07767403.4.

* cited by examiner

*Primary Examiner* — Jason M Nolan
(74) *Attorney, Agent, or Firm* — Sughrue Mion, PLLC

(57) ABSTRACT

A method for producing crystal A of 2-(3-cyano-4-isobutyloxyphenyl)-4-methyl-5-thiazolecarboxylic acid by dissolving 2-(3-cyano-4-isobutyloxyphenyl)-4-methyl-5-thiazolecarboxylic acid in methanol or a mixed solvent of methanol and water (the volume ratio of methanol to water is 90/10 or more), then adding water until the ratio of methanol to water becomes 7/3, and further adding a specific amount of a seed crystal at a specific timing during the addition of water.

1 Claim, 2 Drawing Sheets

METHOD FOR PRODUCING CRYSTAL POLYMORPHS OF 2-(3-CYANO-4-ISOBUTYLOXYPHENYL)-4-METHYL-5-THIAZOLECARBOXYLIC ACID

TECHNICAL FIELD

The present invention relates to a method for producing crystal A of 2-(3-cyano-4-isobutyloxyphenyl)-4-methyl-5-thiazolecarboxylic acid. This compound has an action of regulating biosynthesis of uric acid in vivo and can be used as a therapeutic agent for hyperuricemia.

BACKGROUND ART

In the production of a drug, it is critical to regulate crystal polymorphism of a chemical substance, an ingredient thereof, because differences in crystalline forms greatly affect properties of the drug such as performance of a preparation, bioavailability, and stability as described in the International Conference on Harmonization (ICH) Q6A Guideline, "Specifications: Test Procedures and Acceptance Criteria for New Drug Substances and New Drug Products: Chemical Substances."

Patent Document 1 discloses the presence of five crystal polymorphs of 2-(3-cyano-4-isobutyloxyphenyl)-4-methyl-5-thiazolecarboxylic acid, crystals A, B, C, D, and G and an amorphous form and a method for producing them. The method for producing crystal polymorphs described here involves the production of each crystal polymorph by adding a predetermined mixed solvent of methanol and water to 2-(3-cyano-4-isobutyloxyphenyl)-4-methyl-5-thiazolecarboxylic acid, dissolving the resultant mixture by heating with stirring, cooling the mixture by the addition of water to obtain the predetermined methanol and water composition and temperature, then collecting crystals by filtration, and drying the crystals.

However, effects of the initial concentration presented in the aforementioned invention are only mentioned with regard to chemical purity and yield in the "Disclosure of the Invention," and the effects on crystal polymorphs obtained are not mentioned.

At the International Symposium on Industrial Crystallization (Sep. 21-25, 1998, Tianjin, China), Kitamura, Hanada, Nakamura, and others showed in "Crystallization and transformation behavior of thiazole-derivative" that, when the time for water addition is markedly changed, in some cases crystal G or a mixture of crystals A and G may be obtained upon crystallization with the methanol-water composition and the temperature that were thought to result in the formation of only crystal A, and that the crystals obtained are converted to crystal D by changing the temperature and then maintaining it with stirring.

In the production of industrially useful crystal A, the possibility cannot be ruled out that crystal G may be incorporated in these conventional methods. Since the time for water addition is restricted in order to prevent incorporation of crystal G, there is also a problem that industrial production is time-consuming.

Meanwhile, Patent Document 2 discloses a method for producing crystal A or G or a mixture of crystals A and G of 2-(3-cyano-4-isobutyloxyphenyl)-4-methyl-5-thiazolecarboxylic acid, comprising changing the initial concentration and the time for water addition in producing a crystal polymorph by adding water to 2-(3-cyano-4-isobutyloxyphenyl)-4-methyl-5-thiazolecarboxylic acid dissolved in methanol or a mixed solvent of methanol and water.

However, by crystallization using this mixed solvent system, a crystalline form that is not crystal A or a mixture with crystal A was obtained, and crystal A was not stably obtained, when the ratio of methanol to water was 7:3, the solvent composition used in the present invention.

According to the present invention, it was found that crystal A was obtained even in a region off "region I" in Patent Document 1 when a seed crystal of crystal A was used in a region off "region I" under specific conditions. While crystallization using a seed crystal has been achieved using other solvent compositions, there has been no example in which the solvent composition of the present invention was used.

Patent Document 1: International Publication No. WO99/65885

Patent Document 2: Japanese Patent Laid-Open Publication No. 2003-261548

DISCLOSURE OF THE INVENTION

An object of the present invention is to selectively provide crystal A of 2-(3-cyano-4-isobutyloxyphenyl)-4-methyl-5-thiazolecarboxylic acid under conditions that are also suitable for industrial production.

The foregoing object is attained by a method for producing crystal A, comprising dissolving 2-(3-cyano-4-isobutyloxyphenyl)-4-methyl-5-thiazolecarboxylic acid in methanol or a mixed solvent of methanol and water having a volume ratio of methanol to water of 90/10 or more, adding water until the ratio of methanol to water becomes 7/3, and adding a specific amount of a seed crystal (crystal A) at a specific timing during the addition of water, the amount of the seed crystal to be added and the timing of adding the seed crystal being defined by a condition shown in region I in FIG. 1 when the initial concentration is 0.024±0.008 mol/L and the water addition rate is 0.007 mL/min/mL, the amount of the seed crystal to be added and the timing of adding the seed crystal being defined by a condition shown in region I in FIG. 2 when the initial concentration is 0.024±0.008 mol/L and the water addition rate is 0.01175 mL/min/mL, or the amount of the seed crystal to be added and the timing of adding the seed crystal being defined by a condition corresponding to region I obtained by interpolating these two conditions in proportion to the water addition rate.

Hereafter, the expression "a condition corresponding to region I obtained by interpolating these two conditions in proportion to the water addition rate" will be explained. For example, the lower right vertex of a rectangular region shown as region I in FIG. 1 has a coordinate (1.25 mg/mL, 40 min), and that of the corresponding vertex in FIG. 2 is (1.25 mg/mL, 25 min). Assuming that the coordinate of a vertex at a water addition rate of 0.010 mL/min/mL is to be obtained, the X coordinate is 1.25 mg/mL, and the Y coordinate is 40 min+(25 min−40 min)×(0.010 mL/min/mL−0.007 mL/min/mL)/(0.01175 mL/min/mL−0.007 mL/min/mL) about 30.5 min. Since the remaining three vertices are similarly obtained, the corresponding condition in region I at the water addition rate can be easily established.

When this is further generalized, the coordinates (amount of a seed crystal to be added [mg/mL], timing for adding seed crystal [min]) of the four vertices of a rectangle corresponding to region I at a water addition rate of r (mL/min/mL, $0.007 < r < 0.01175$) are as follows.

Upper left vertex: 0.25+(r−0.007)/(0.01175−0.007)×(0.41−0.25) (mg/mL), 50+(r−0.007)/(0.01175−0.007)×(30−50) (min)

Lower left vertex: 0.25+(r−0.007)/(0.01175−0.007)×(0.41−0.25) (mg/mL), 40+(r−0.007)/(0.01175−0.007)×(25−40) (min)

Upper right vertex: 1.25 (mg/mL), 50+(r−0.007)/(0.01175−0.007)×(30−50) (min)

Lower right vertex: 1.25 (mg/mL), 40+(r−0.007)/(0.01175−0.007)×(25−40) (min)

The above-mentioned values are obtained by the interpolation based on the numerical value of a water addition rate, and may be extrapolated to a range of r<0.007 and r>0.01175 (unit, mL/min/mL) so long as the object of the present invention is attained. In this case, since other specific conditions can be easily calculated based on a water addition rate under suitably established preset conditions, whether the range of extrapolation attains the object of the present invention can be easily determined by those skilled in the art by trial runs.

That is, the present invention was accomplished based on the finding that, by allowing a specific amount of a seed crystal to act at a specific timing, crystal A can be obtained with a solvent composition which has never been thought conventionally to result in obtaining crystal A.

The expression "crystal A of 2-(3-cyano-4-isobutyloxyphenyl)-4-methyl-5-thiazolecarboxylic acid" used herein means a crystal polymorph which shows an X-ray powder diffraction pattern having characteristic peaks approximately at 6.62°, 7.18°, 12.80°, 13.26°, 16.48°, 19.58°, 21.92°, 22.68°, 25.84°, 26.70°, 29.16°, and 36.70° as expressed by the reflection angle of 2θ. Alternatively, this crystal can be expressed as a crystal polymorph showing characteristic absorption distinguishable from other crystal polymorphs in the vicinity of 1678 cm$^{-1}$ in infrared absorption spectroscopy. Refer to the specification of International Publication No. WO99/65885.

The present invention has an effect that crystal A can be selectively obtained by adding a seed crystal although a solvate or a mixture of a solvate and a hydrate are obtained without a seed crystal. More specifically, this method has an advantage that crystal A can be selectively obtained at 40° C. or lower, at which a methanolated substance or a hydrate is precipitated with a conventional technique. Specifically, according to the present invention, crystal A of 2-(3-cyano-4-isobutyloxyphenyl)-4-methyl-5-thiazolecarboxylic acid can be produced under conditions suitable for industrial production while reducing the possibility of incorporation of other crystal polymorphs.

BEST MODE FOR CARRYING OUT THE INVENTION

Figure 1:
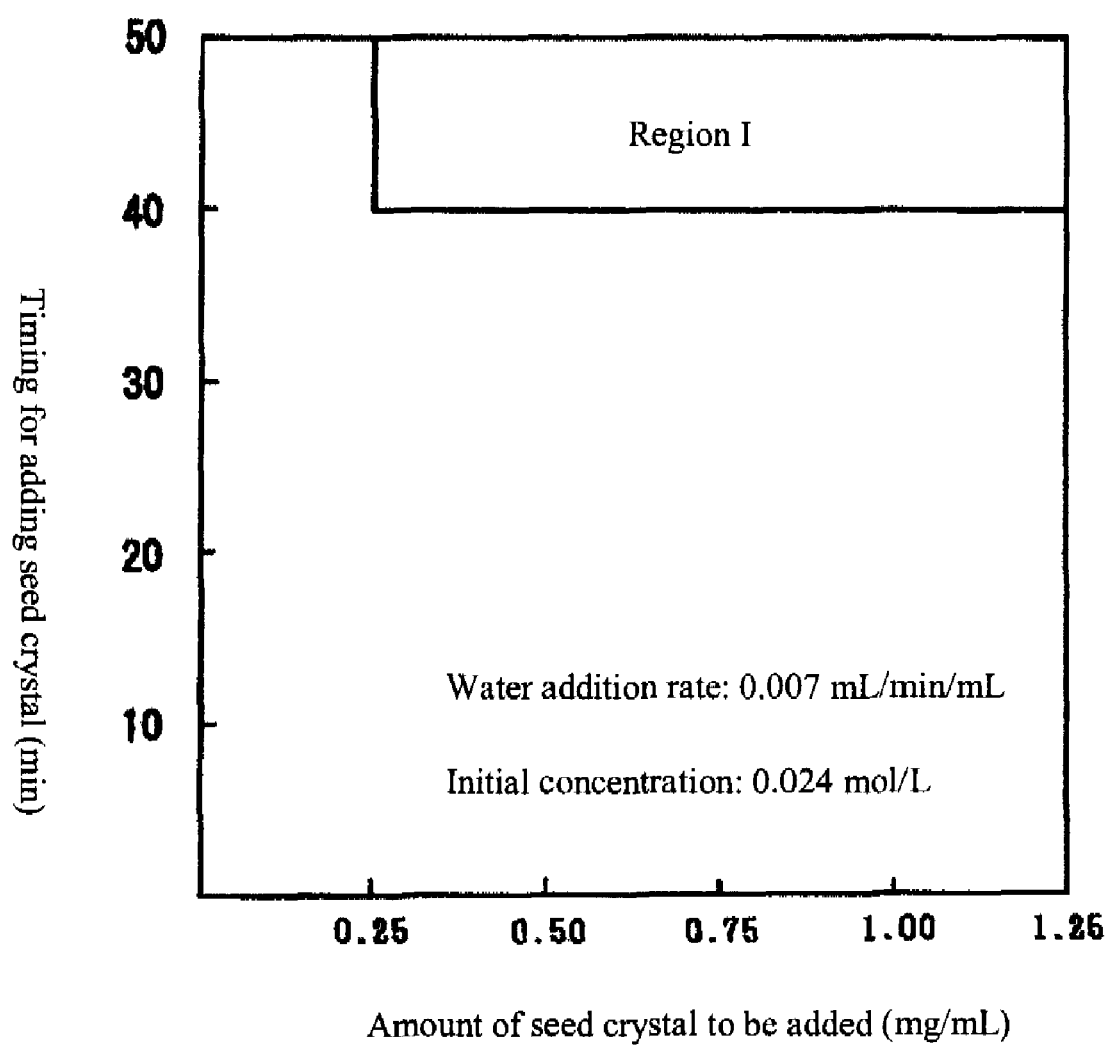
FIG. 1 is an example of diagrams showing the conditions of amount of seed crystal to be added, timing for adding a seed crystal, and water addition rate in the production method of the present invention.
Figure 2:
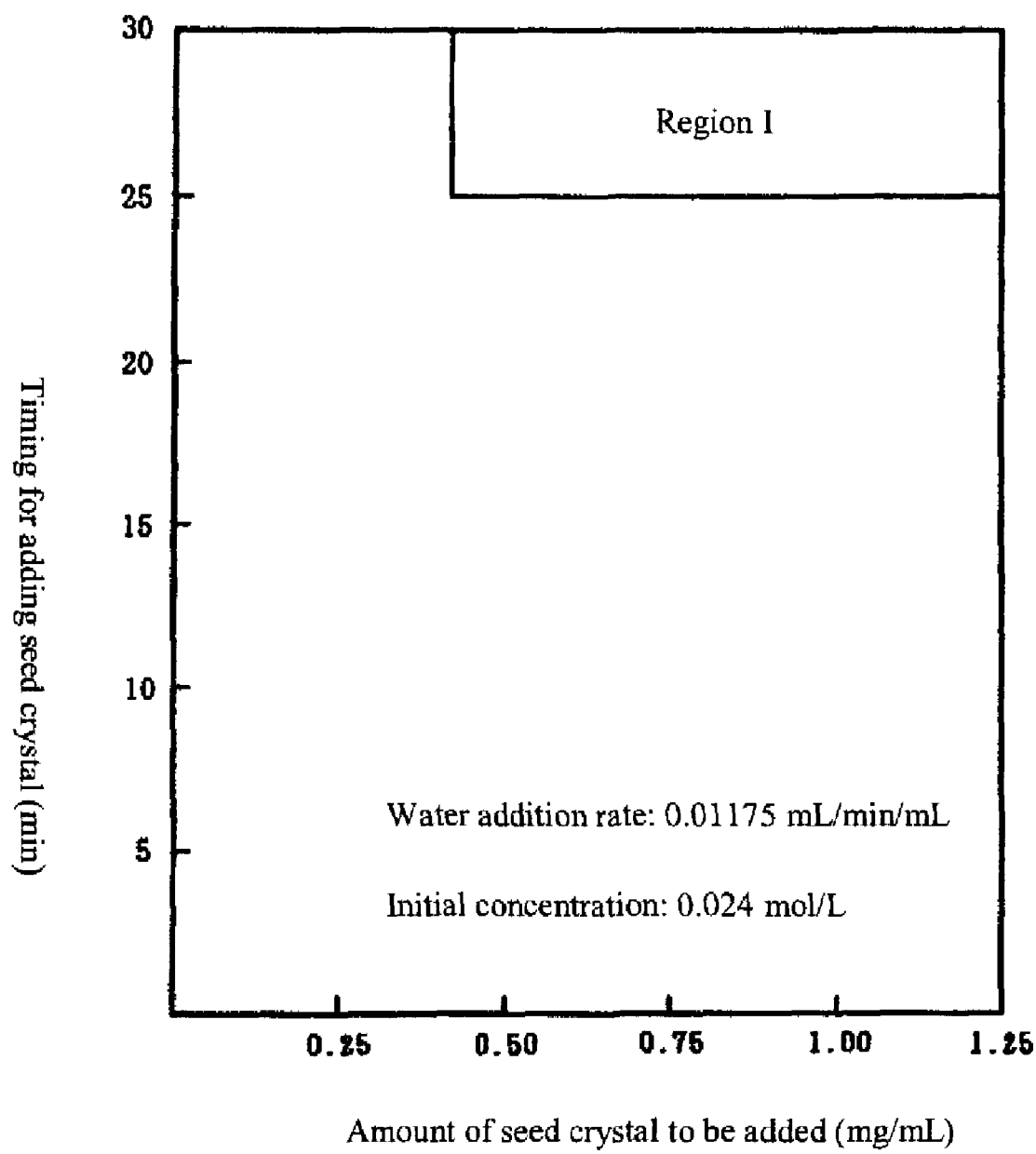
FIG. 2 is an example of diagrams showing the conditions of amount of seed crystal to be added, timing for adding a seed crystal, and water addition rate in the production method of the present invention.

Firstly, the composition ratio of methanol to water at the time of dissolution is methanol/water=90/10 (volume (L) ratio, same below) or more, and is preferably in the range of methanol/water=100/0 to 95/5. Of all, the range of 97/3 to 95/5 is more preferred, and 95/5 is particularly preferred.

Secondly, the initial concentration of a solute is preferably in the of range 0.024±0.008 mol/L. Of all, the range of 0.024±0.004 mol/L is more preferred, and 0.024 mol/L is particularly preferred.

Furthermore, the amount of a seed crystal to be added to each initial solution is preferably 20 mg/40 mL or more.

Furthermore, the water addition rate is preferably in the range 0.25 to 0.50 mL/min based on 40 mL of a solution before addition.

When the amount of the initial solution is not 40 mL, preferable amounts of the seed crystal to be added and water addition rates are determined in proportion to the amount of the initial solution based on the above-mentioned values.

EXAMPLE

The present invention will be explained more specifically with reference to the following example. However, the scope of the present invention is not limited to this example.

Example 1

0.024 mol/L of a solution of 2-(3-cyano-4-isobutyloxyphenyl)-4-methyl-5-thiazolecarboxylic acid in methanol and water (95:5) was prepared, and 14.2 mL of water was added to 40 mL of the mixture at a rate of 0.28 mL/min while maintaining the inside temperature at 40° C. During the addition of water, 10 mg of a seed crystal (crystal A) was added after a lapse of 40 min. Precipitated crystals were collected by filtration and then dried. When the powder X-ray diffraction of the obtained crystals was analyzed, these crystals were found to be crystal A. Further, when the amount of the seed crystal added was changed from 20 mg to 40 mg, crystal A was similarly obtained.

INDUSTRIAL APPLICABILITY

The crystal A of 2-(3-cyano-4-isobutyloxyphenyl)-4-methyl-5-thiazolecarboxylic acid obtained the production method of the present invention is used as a drug.

The invention claimed is:

1. A method for producing crystal A of 2-(3-cyano-4-isobutyloxyphenyl) -4-methyl-5-thiazolecarboxylic acid, comprising dissolving 2-(3-cyano-4-isobutyloxyphenyl)-4-methyl-5-thiazolecarboxylic acid in methanol or a mixed solvent of methanol and water having a volume ratio of methanol to water of 90/10or more, adding water until the ratio of methanol to water becomes 7/3, and adding a specific amount of a seed crystal at a specific timing during the addition of water, wherein the amount of the seed crystal to be added is not less than 0.25 +(r−0.007)/(0.01175−0.007)×(0.41−0.25) (mg/mL) and not more than 1.25 (mg/mL), and the timing of adding the seed crystal is not earlier than 40+(r−0.007)/(0.01175−0.007)×(25−40) (min) and not later than 50+(r—0.007)/(0.01175−0.007)×(30−50) (min), when the initial concentration of 2-(3-cyano-4-isobutyloxyphenyl)-4-methyl-5-thiazolecarboxylic acid is 0.024 ±0.008 mol/L and the water addition rate (r) is 0.007mL/min/mL $\leqq$ r $\leqq$ 0.01175 mL/min/mL.

* * * * *